United States Patent

Uchida et al.

[11] Patent Number: 5,844,661
[45] Date of Patent: Dec. 1, 1998

[54] OPHTHALMIC APPARATUS

[75] Inventors: Saeko Uchida, Okayama; Yasuo Kato; Takeshi Nakamura, both of Tokyo, all of Japan

[73] Assignee: Kabushiki Kaisha, TOPCON, Tokyo, Japan

[21] Appl. No.: 911,977

[22] Filed: Aug. 15, 1997

[51] Int. Cl.$^6$ ........................................................ A61B 3/10
[52] U.S. Cl. ........................................... 351/211; 351/221
[58] Field of Search .................................... 351/211, 212, 351/206, 205, 221, 246, 247

[56] References Cited

U.S. PATENT DOCUMENTS 5,612,754  3/1997  Tanaka ...................................... 351/211

Primary Examiner—Hung X. Dang
Attorney, Agent, or Firm—Oppedahl & Larson

[57] ABSTRACT

An objective refraction measuring system of an ophthalmic apparatus measures a refractive power of an eye to be examined in an objective manner under the condition that a gazing chart of a gazing target system is fixed to the eye to be examined. An arithmetic-logic unit obtains an objective measurement value of the eye to be examined on the basis of the measurement result by the objective refraction measuring system and the gazing target system. A control unit controls a continuous objective measurement while fogging the gazing chart after setting the gazing chart of the gazing chart system to a far-sight position of the eye to be examined which is obtained by using the gazing target system. With such measurement, the continuous objective measurement values by fogging the gazing chart of the gazing target system is obtained from the far-sight position based upon the objective measurement of the eye to be examined. Thus, the limit of the adjustment force of the eye to be examined is precisely measured.

8 Claims, 9 Drawing Sheets

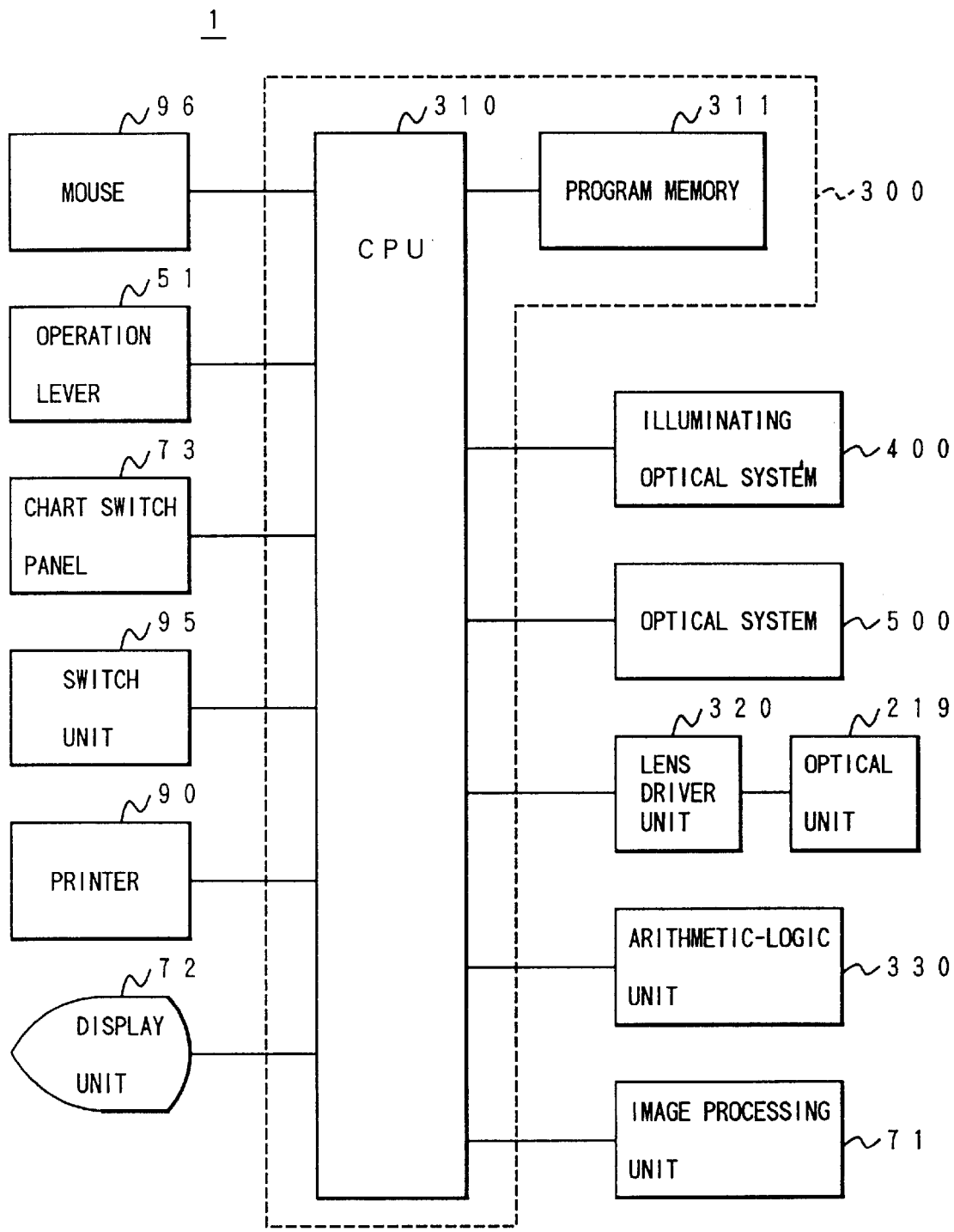
F I G. 7

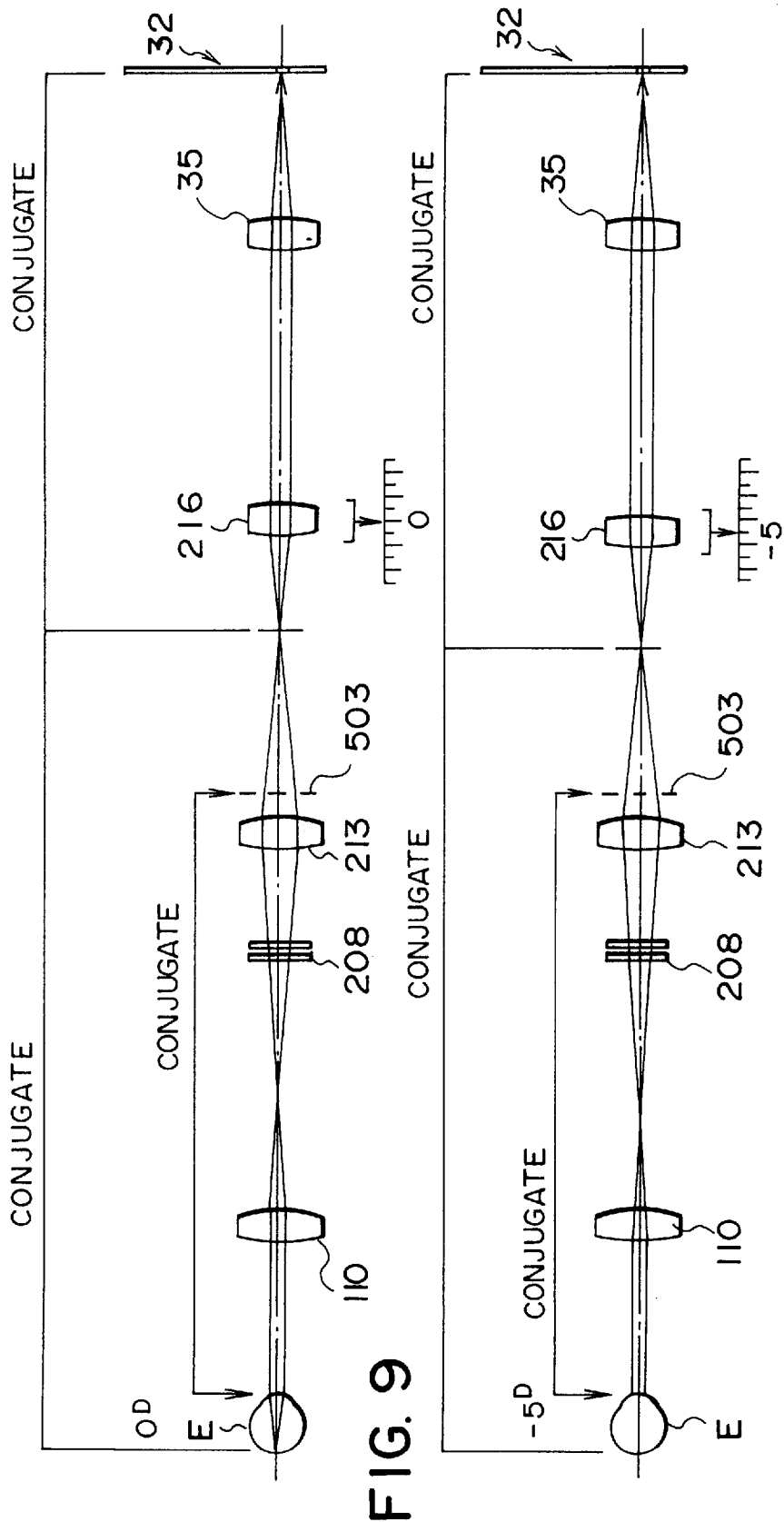

| | AMOUNT OF FOGGING | OBJECTIVE MEASUREMENT RESULTS |
|---|---|---|
| 1 | S-0.25  C-0.50  A180 | S-0.25  C-0.50  A180 |
| 2 | S-0.00  C-0.50  A180 | S-0.00  C-0.50  A180 |
| 3 | S+0.25  C-0.50  A180 | S-0.00  C-0.50  A180 |
| 4 | S+0.50  C-0.50  A180 | S-0.00  C-0.50  A180 |

FIG. 11

| | AMOUNT OF FOGGING | OBJECTIVE MEASUREMENT RESULTS |
|---|---|---|
| 1 | S-0.25 | S-0.25  C-0.50  A180 |
| 2 | S-0.00 | #S-0.00  C-0.50  A180 |
| 3 | S+0.25 | S-0.00  C-0.50  A180 |
| 4 | S+0.50 | S-0.00  C-0.50  A180 |

FIG. 12

OPHTHALMIC APPARATUS

BACKGROUND OF THE INVENTION

1. Field of the Invention

The present invention relates to an ophthalmic apparatus which may enable the selection of a spectacle lens suitable for an eye to be examined through an objective measurement to the eye.

2. Description of Related Art

For example, in a conventional ophthalmic apparatus for measuring a variety of eye functions such as a visual acuity and an astigmatism of an eye to be examined in an objective manner, the examining person such as an optometrist operates the operation unit of the objective refraction measuring apparatus while watching the image monitor, and then an alignment/positioning of the eye to be examined is performed while observing a desired chart, so that objective measurement values such as a spherical degree or the like of the eye to be examined are obtained.

However, in the conventional ophthalmic apparatus, since the alignment/positioning of the eye to be examined is carried out by simply rendering the eye to observe the desired chart and the objective measurement values such as the spherical degree or the like of the eye to be examined are automatically measured and calculated to obtain them, the objective measurement values such as the spherical degree involves the error to some extent. Thus, there is a problem that it is impossible to obtain the measurement values of the eye to be examined in precision.

SUMMARY OF THE INVENTION

In view of the foregoing difficulties, an object of the present invention is to provide an ophthalmic apparatus which may realize the precise measurement for the objective measurement values of the eye to be examined and which enables the selection of the ophthalmic lens suitable for the eye to be examined.

According to the present invention, there is provided an ophthalmic apparatus comprising: an objective refraction measuring system for measuring a refractive power of an eye to be examined in an objective manner; a gazing target system having a gazing chart fixed to the eye;means for detecting a far-sight position of the eye by the gazing target system; and fogging means for setting the gazing chart to the detected far-sight position and fogging the set gazing chart, wherein a continuous objective measurement is performed by the objective refraction measuring system while fogging the set gazing chart by the fogging means.

According to the present invention, there is provided an ophthalmic apparatus comprising: objective measuring means for measuring objective measurement values of an eye to be examined; gazing chart fixing means for fixing a gazing chart to the eye; means for detecting a far-sight position of the eye by the gazing chart fixing means; fogging means for setting the gazing chart to the detected far-sight position of the eye and fogging the set gazing chart by desired fogging amounts, to perform a continuous objective measurement by the objective measuring means; and output means for outputting the fogging amounts of the gazing chart in the continuous objective measurement and the objective measurement values measured by the objective measuring means.

The objective refraction measuring system of the ophthalmic apparatus according to the present invention measures the refraction power of the eye to be examined in an objective manner under the condition that the gazing chart of the gazing target system is fixed to the eye.

The objective measurement values are obtained in accordance with the measurement result by the objective refraction measuring system and the gazing target system.

After the gazing chart of the gazing target system is set into the far-sight position of the eye to be examined which is obtained by the gazing target system, the continuous objective measurement is performed by fogging the gazing chart.

By such measurement, continuous objective measurement values which can be obtained by fogging the gazing chart of the gazing target system from the far-sight position based on the objective measurement of the eye to be examined, so that the limit of the adjustment force of the eye can be measured precisely.

In the ophthalmic apparatus according to the present invention, in addition to the operation of the above mentioned ophthalmic apparatus, since the output means visually outputs the fogging amount of the gazing chart with the continuous objective measurement and measurement results of the objective refraction measuring system, a subjective comfortable degree for a spectacle lens to be treated can be estimated in accordance with spherical degrees that values of measurement results of the objective refraction measuring system output from the output means are constant. Thus, the precise objective measurement of the eye to be examined is realized, and further a spectacle lens suitable for the eye to be examined can be selected based on the subjective comfortable degree.

BRIEF DESCRIPTION OF THE DRAWINGS

FIG. 7 shows a block diagram of a control system of the ophthalmic apparatus according to the embodiment;

FIG. 9 is a view of an optical arrangement in the case where the spherical degree is at zero diopter (0D) in the ophthalmic apparatus according to the embodiment;

FIG. 10 is a view of an optical arrangement in the case where the spherical degree is at −5 diopter (−5D) in the ophthalmic apparatus according to the embodiment;

FIG. 11 shows a relationship between the fogging amount and the objective measurement result in the ophthalmic apparatus according to the embodiment; and FIG. 12 shows an example of a print presenting the relationship between the fogging amount and the objective measurement result in the ophthalmic apparatus according to the embodiment.

DETAILED DESCRIPTION OF THE PREFERRED EMBODIMENTS

An embodiment of the invention will now be described in detail with reference to the accompanying drawings.

Figure 1:
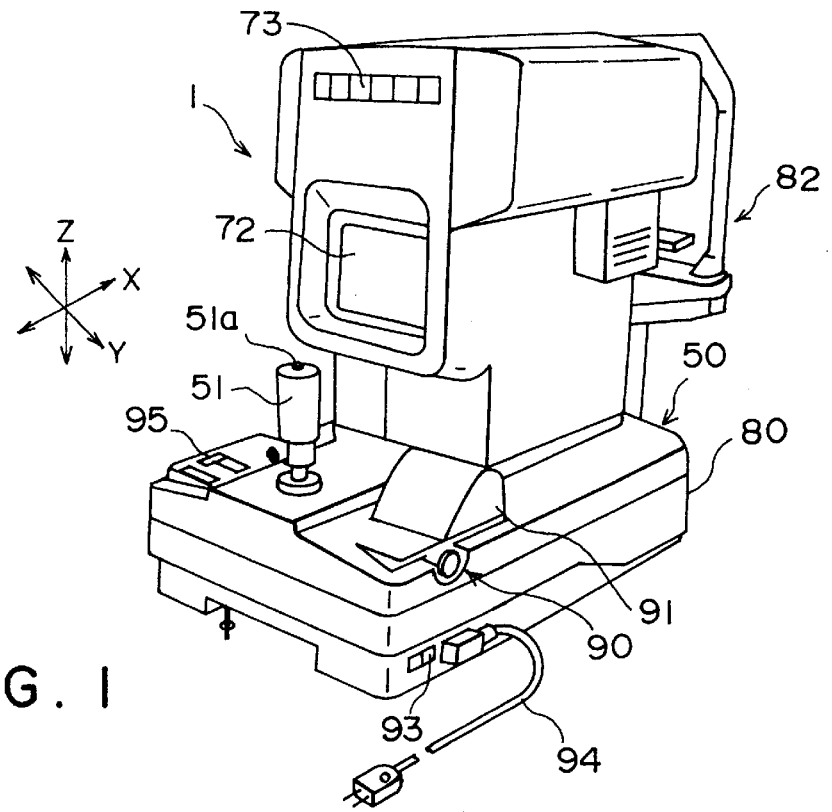
FIG. 1 shows an ophthalmic apparatus as viewed from the examiner in accordance with an embodiment of the present invention.
Figure 2:
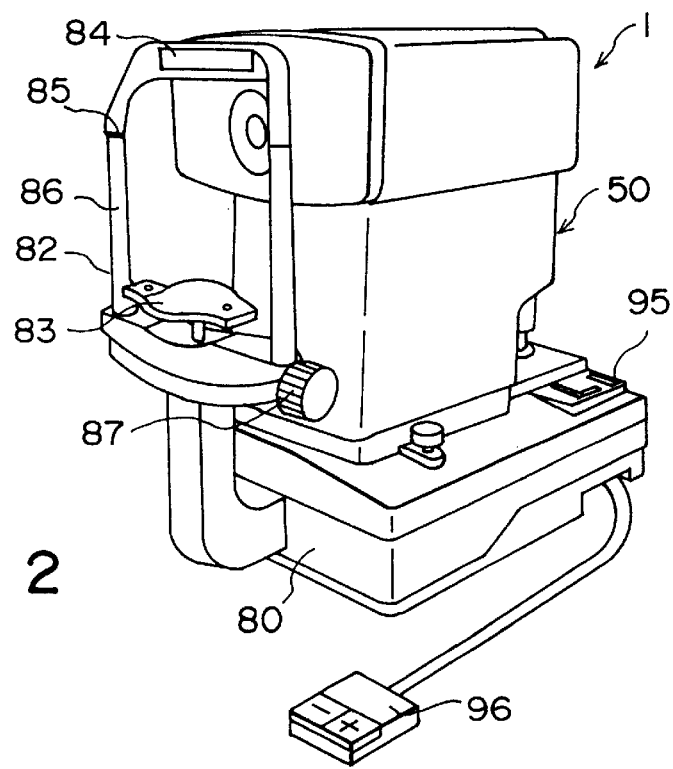
FIG. 2 shows the ophthalmic apparatus as viewed from the person to be examined in accordance with the embodiment.

An ophthalmic apparatus 1 according to the embodiment of the invention as shown in FIGS. 1 and 2 is provided with a box-shaped apparatus body 50. The apparatus body 50 may be moved on a base table 80 in any direction of X, Y and Z by the operation of an operation handle 51 constituting an operation unit provided with an operation switch 51a.

A jaw receiving base 82 on which jaws of a person to be examined are to be placed is provided on one edge side of the apparatus body 50. The jaw receiving base 82 is provided with a jaw receiver 83, a forehead contact 84, a post 86 having a height mark 85, a jaw receiving handle 87 and the like.

Figure 4:
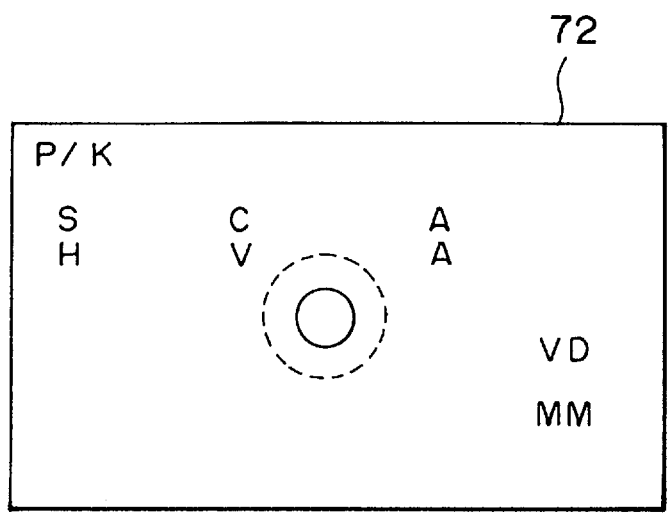
FIG. 4 shows a display example of a display unit of the ophthalmic apparatus according to the embodiment.

A display unit 72 for displaying a front eye portion image of the eye E to be examined, a corneal reflective image, various measurement values, a defocus confirmation image or the like, as shown in FIG. 4, is provided in the other edge side of the apparatus body 50.

Figure 3:
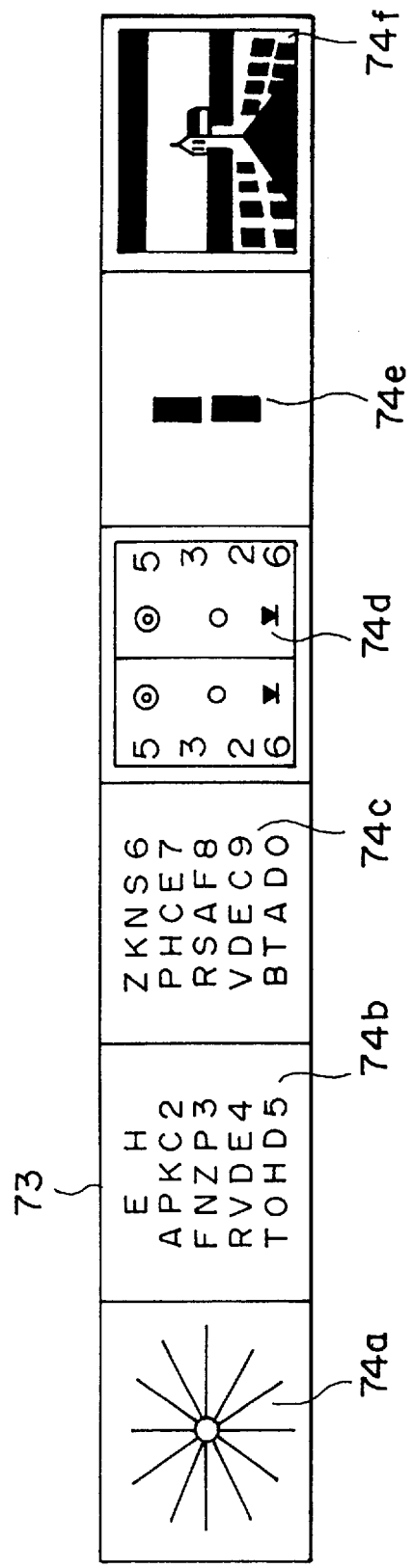
FIG. 3 shows a chart switch panel of the ophthalmic apparatus according to the embodiment.

A chart switch panel 73 constituting the operation unit is provided in the upper portion of the display unit 72. As shown in FIG. 3, the chart switch panel 73 has a star burst chart switch 74a, a visual acuity chart switch 74b and 74c, a red/green chart switch 74d, a separate chart switch 74e and a picture chart switch 74f.

As shown in FIG. 1, a printer 90 constituting an output unit provided with a printer cover 91 is disposed on the other end side of the apparatus body 50, and a power supply switch 93 and a power supply line 94 are provided. Also, in the other end side of the apparatus body 50, there is provided a switch unit 95 constituting the operation unit which includes a mode selection switch for the subjective measurement or the objective measurement, an addition power measurement switch, a dip switch, an automatic starting switch, a print switch and the like. In the one end side of the apparatus body 50, a mouse 96 constituting the operation unit and may be manipulated by the person to be examined is provided.

An optical arrangement for the apparatus body 50 will now be described with reference to FIGS. 5 and 6. The apparatus body 50 includes an illuminating optical system 400 for illuminating the eye E of the person to be examined and an optical system 500 for irradiating various rays of light into the eye E and receiving a reflective image from the eye E.

The apparatus body 50 including the illuminating optical system 400 and the optical system 500 will now be described in detail.

The optical system 500 of the apparatus body 50 is composed of: a corneal measuring system 1A for measuring a radius of curvature of a cornea C of the eye E to be examined; an objective refractive measuring system 2 for measuring the refractive power of the eye E to be examined in the objective manner; a gazing target system 3 for projecting various charts such as a separate chart 501 (to be described later), a picture chart and a star burst chart which are a gazing chart for fixing the eye E to fix a visual axis of the eye to be examined during the measurement, and a visual acuity chart and a red/green chart for the subjective measurement; and an observation/alignment system 4 for performing the front eye portion observation of the eye E and the alignment between the optical axis of the optical system 500 and the visual axis of the eye E. A portion of the optical path of the observation/alignment system 4 is common with the optical path of the corneal measuring system 1A.

The corneal measuring system 1A has a pattern projection system 10 for projecting an annular pattern to the cornea C to measure the radius of curvature of the cornea C of the eye to be examined and a measuring optical system 11 for measuring a size and a shape of the corneal reflective image of the annular pattern.

The pattern projection system 10 is composed of a pattern plate 101 having an annular opening 100 and an annular light source 102 which is disposed behind the opening 100 and emits corneal measuring light having a wavelength of 930 to 1,000 nm.

The light emitted from the annular light source 102 is projected through the annular opening 100 to the cornea C of the eye E as the projecting light. The projecting light forms a virtual image of the annular opening 100 in the cornea C. The corneal measuring light reflected by the cornea C is incident on the measuring optical system 11 as if the virtual image would be projected.

The measuring optical system 11 is composed of an objective lens 110, a mirror 111 which reflects the visual light having the wavelength of 400 to 700 nm and passes the light in the long wavelength region not shorter than 800 nm including the corneal measuring light (wavelength of 930 to 1,000 nm), a mirror 112 which passes an infrared light having a wavelength of 865 nm and reflects the infrared light having a wavelength of 900 nm or more, a relay lens 113, a diaphragm 114, a mirror 115 which passes a red light having the wavelength of 700 nm but reflects the corneal measuring light, a relay lens 116, a mirror 117 which reflects the infrared light having the wavelength of 865 nm but passes the corneal measuring light and the red light having the wavelength of 700 nm, an imaging lens 118, and a light receiving element 5 such as an area CCD or an imaging tube. A detection signal of the light receiving element 5 is processed by an image processing unit 71 and then is transferred to the display unit 72 under the control of a control unit to be described later.

After the corneal measuring light reflected by the cornea C is collected by the objective lens 110, it passes through the mirror 111. The corneal measuring light is reflected by the mirror 112 and passes through a central portion 114b of the diaphragm 114 through the relay lens 113.

The corneal measuring light is reflected by the mirror 115, introduced to the mirror 117 by the relay lens 116, passes through the mirror 117 and projected on the light receiving element 5 by the imaging lens 118 as a corneal measuring ring pattern.

The refractive power measuring light with the wavelength of 865 nm emitted from a light emitting diode 200 constituting the pattern projection system 20 is received by a condenser lens 201. Thereafter, the light is refracted by a conical prism 202 and is irradiated into a ring pattern 203 which also serves as a defocus confirmation pattern for the refractive power measurement.

The refractive power measuring light passed through the ring pattern 203 is irradiated to a ring diaphragm 207 through a relay lens 204, a mirror 205 and a relay lens 206. The refractive power measuring light is passed through the ring diaphragm 207 and then reflected by a reflective surface 208a of a bored mirror 208.

Thereafter, the refractive power measuring light is reflected by the mirror 209, passes through the mirrors 112 and 111 which are structural elements of the measuring optical system 11 of the corneal measuring system 1A, and projected as an image of the ring pattern 203 on the fundus ER of the eye E to be examined by the objective lens 110.

By the way, the light emitting diode 200 and the ring diaphragm 207 are optically conjugative, and at the same time, the ring diaphragm 207 and the pupil of the eye E to be examined are located in an optically conjugative manner.

In the objective refractive measuring system 2, the light of the ring pattern image reflected by the fundus ER of the eye E to be examined is collected by the objective lens 110. After the collected light (refractive power measuring light) is passed through the mirrors 111 and 112, the light is reflected by the mirror 209 and passes through a diaphragm 210 via an opening portion 208b of the bored mirror 208.

The refractive power measuring light passes through the relay lens 211 via the diaphragm 210, reflected by the mirror 212 which passes the visual light, and irradiated to a filter 215 of an optical unit 219 through a relay lens 213 and a mirror 214.

The filter 215 has a peripheral portion 215b which allows the passage of the refractive power measuring light having the wavelength of 865 nm and a central portion 215a which interrupts the refractive power measuring light. Also, the filter 215 has such characteristics that in the overall region, the corneal measuring light having the wavelength of from 930 to 1,000 nm is not passed but the visual light having the wavelength of from 400 to 700 nm is allowed to pass.

Thus, the refractive power measuring light passes only the peripheral portion 215b of the filter 215, and then passes, through a focusing lens 216, a mirror 217 which reflects the visual light and allows the passage of the refractive power measuring light. After that, the refractive power measuring light is reflected by the mirror 117 of the measuring optical system 11 of the corneal measuring system 1A and then irradiated as the ring pattern image (reflective image of defocus confirmation pattern) on the light receiving element 5 by the lens 118 to convert it into an electric signal.

The focusing lens 216 and the filter 215 are provided integrally in the optical unit 219 together with the lightemitting diode 200, the condenser lens 201, the conical prism 202 and the ring pattern 203 of the pattern projection system 20. The optical unit 219 is movable along an optical axis direction and moved along the optical axis direction by a lens driver unit to be described later.

In the objective refractive measuring system 2, the diaphragm 210 is optically conjugative with a position of the pupil of the eye E to be examined with respect to the objective lens 110. Also, the light receiving element 5 is optically conjugative with an intermediate imaging surface of the ring pattern 203 when the eye E is in an emmetropia (refractive power is zero diopter).

The visual light having the wavelength of 400 to 700 nm emitted from the light source 30 of the gazing target system 3 is collected by a condenser lens 31 to illuminate the chart board 32.

Figure 5:
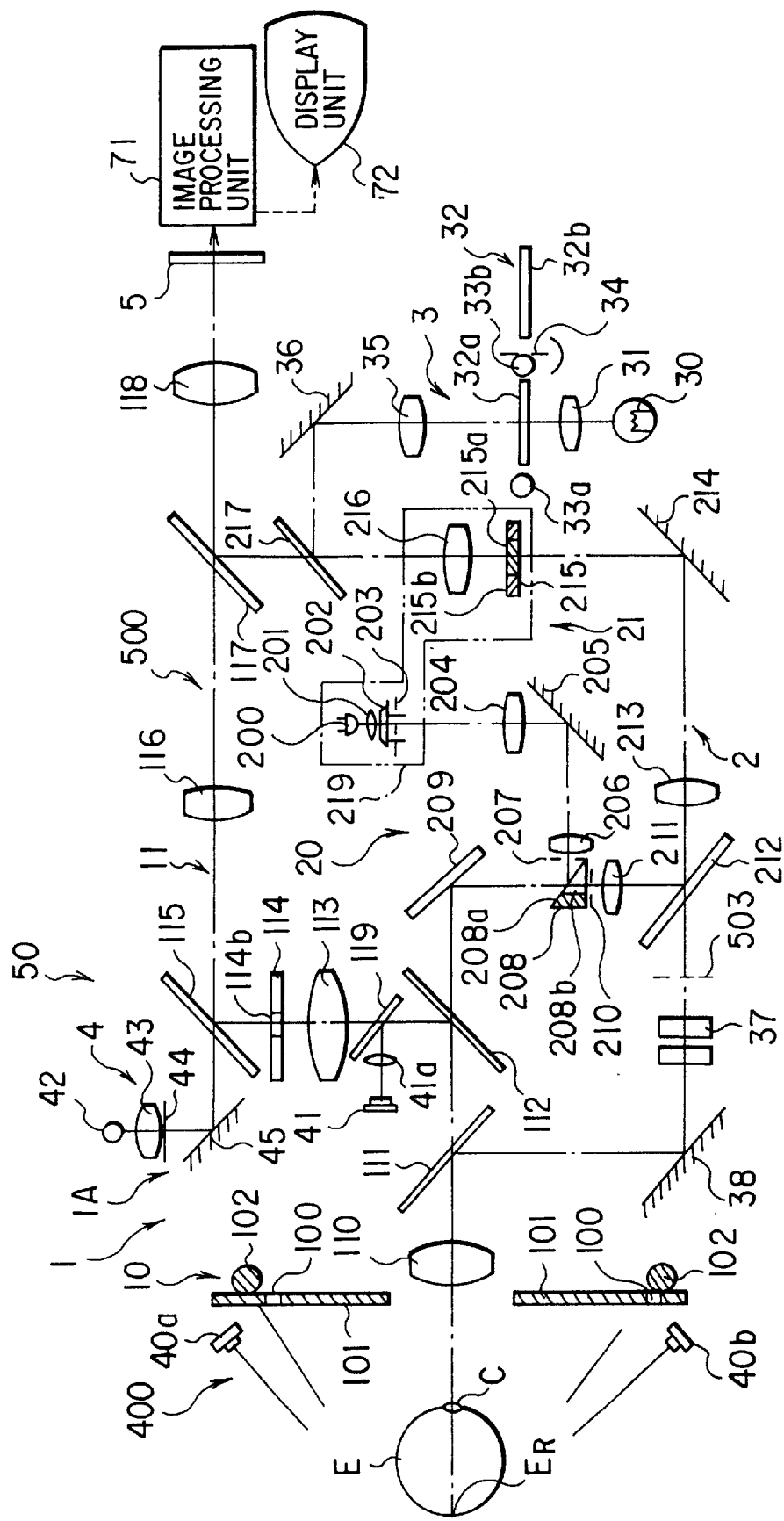
FIG. 5 shows an optical arrangement of the ophthalmic apparatus according to the embodiment.

In the chart board 32 (FIG. 5 shows chart boards 32a and 32b), the star burst chart, the visual acuity chart for the subjective inspection, the separate chart 501 of rad/green and the like are arranged in the circumferential direction. Each chart may be selectively interposed in the optical path of the gazing target system 3 by rotating the chart board 32 around an axis 34.

The light passed through the star burst chart, the separate chart 501 or the like passes the projection lens 35, and then is reflected by the mirror 36. Thereafter, the light is reflected by the mirror 217 and merged into the measuring optical system 21 of the objective refractive measuring system 2. Also, the light passes the filter 215 through the focusing lens 216 and is introduced into the mirror 212 through the mirror 214 and the relay lens 213. The light passed through the mirror 212 is further introduced into a variable cross cylinder 37 through a diaphragm (pupil dividing diaphragm) 503 having a pair of through holes 503a and 503b corresponding to a pair of separately arranged marks 501a and 501b constituting the separate chart 501 shown in FIG. 6.

Figure 6:
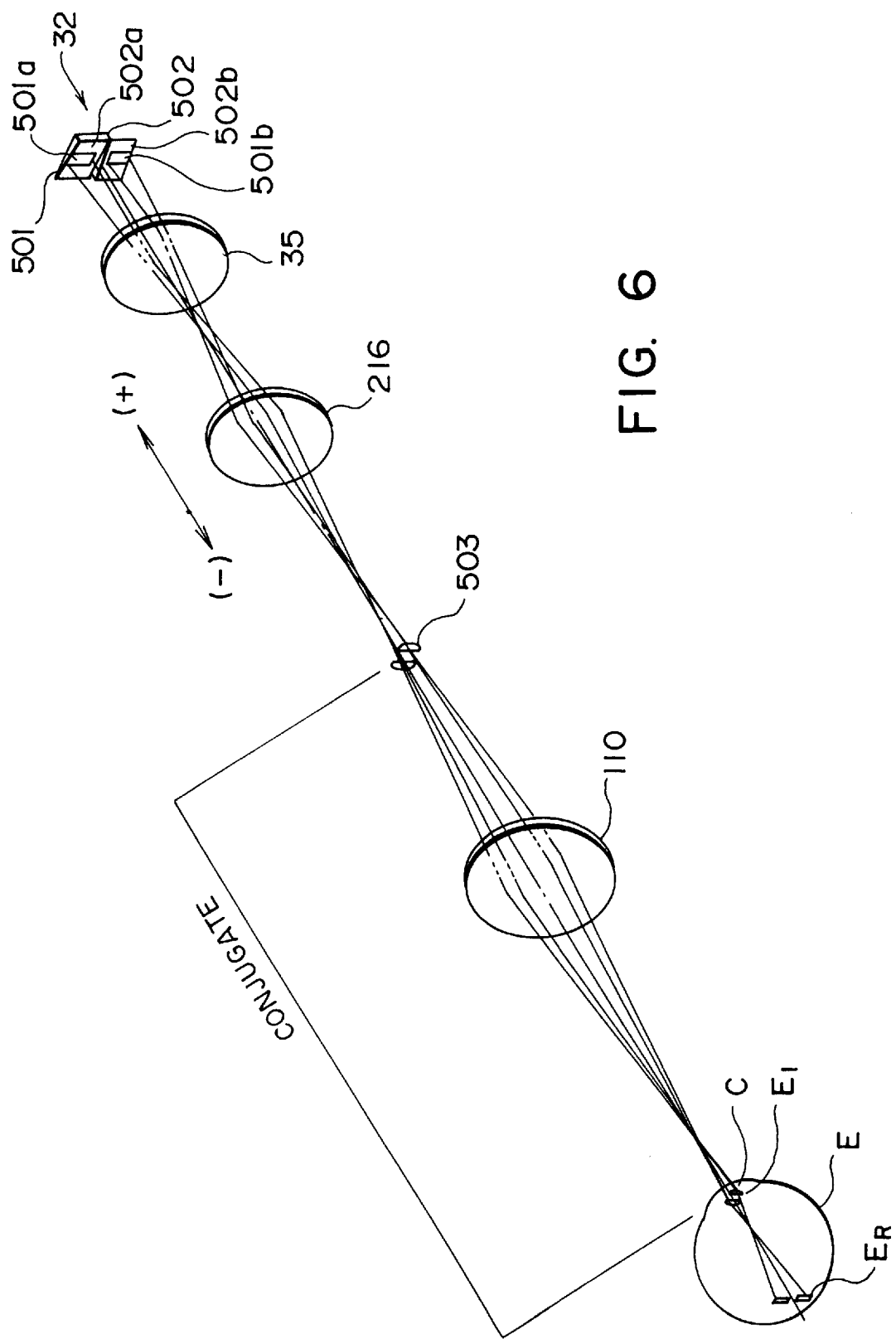
FIG. 6 shows an optical arrangement for projecting the separate chart to the eye in the ophthalmic apparatus according to the embodiment.

As shown in FIG. 6, the pair of separately arranged marks 501a and 501b of the separate chart 501 are attached to a central portion of a split prism 502 composed of a pair of prisms 502a and 502b arranged so that their oblique directions are opposite to each other and their oblique angles are the same.

The light passed through the variable cross cylinder 37 is reflected by a mirror 38 and a mirror 111, projected to the eye E to be examined by the objective lens 110 and observed by the eye E to be examined.

The separate chart 501 and the fundus ER of the eye E to be examined are set in conjugative relation with each other when the eye E is in the emmetropia. The diaphragm 503 and the pupil EI of the eye E to be examined are set in conjugative relation with each other.

A plurality of glare light sources 33a and 33b for emitting the visual light for the glare test are disposed in the vicinity of the chart board 32. The glare light sources 33a and 33b may be disposed near the objective lens 110. Also, for the glare test, instead of providing the glare light sources 33a and 33b, for example, it is possible to use a structure for changing the contrast between the visual acuity chart and the base of the chart board 32.

A plurality of light emitting diodes 40a and 40b for illuminating the front eye portion are arranged outside of the pattern plate 101 of the pattern projection system 10 of the corneal measuring system 1A, so that the infrared light having the wavelength of 900 nm emitted from each of the light emitting diodes 40a and 40b is illuminated into the front eye portion of the eye E to be examined.

After the light reflected at the front eye portion of the eye E to be examined is collected by the objective lens 110, it passes the mirror 111 and is then transmitted along the measuring optical system 11 of the corneal measuring system 1A to be imaged on the light receiving element 5 by the imaging lens 118.

On the other hand, the light from a focusing/positioning light source 41 which emits the infrared light having a wavelength of 900 nm is projected to the cornea C of the eye E to be examined through a relay lens 41a, a half-mirror 119 and the objective lens 110.

The observation/alignment system 4 is disposed in front of the mirror 115 of the measuring optical system 11 of the corneal measuring system 1A. The observation/alignment system 4 has a light emitting diode 42 for emitting a light (scale light) having a wavelength of 700 nm, a collective lens 43 for collecting the scale light from the light emitting diode 42, and a mirror 45 for reflecting the scale light passed through a sighting scale 44 and for emerging the light into the measuring optical system 11.

The scale light which is passed through the sighting scale 44 and reflected by the mirror 45, is projected on the light receiving element 5 through the measuring optical system 11 by the lens 118 after the passage of the mirror 115. Thus, an alignment circle AR is displayed on the display unit 72, as shown in FIG. 9.

The structure of the control unit for the ophthalmic apparatus 1 will now be described with reference to FIG. 7.

The ophthalmic apparatus 1 has a control unit 300 composed of a CPU (central processing unit) for controlling the overall apparatus and a program memory 311 for storing the control program. Connected to the CPU 310 are the operation lever 51, the display unit 72, the chart switch panel the printer 90, the switch unit 95, and the mouse 96.

The illuminating optical system 400 and the optical system 500 are controlled by the CPU 310. Also, the lens driver unit 320 for moving the optical unit 219 is drive-controlled by the CPU 310. Thus, the focusing lens 216 is moved continuously in a plus (+) direction or a minus direction as shown in FIG. 6.

Further, connected to the CPU 310 is an arithmetic-logic unit 330 for calculating the subjective measurement values, the objective measurement values and the defocus degree of the defocus confirmation pattern, which are measured by the respective optical systems, based upon the results processed through the light receiving element 5 and the image processing unit 71.

The operation of the ophthalmic apparatus 1 will now be described. First of all, the subjective precise measurement of a spherical degree of the eye E to be examined will now be described with reference to FIGS. 8A to 8C and 9.

In case of the subjective precise measurement for the spherical degree of the eye E to be examined, the diaphragm 503 is interposed in the optical path of the objective refractive measuring system 2, and under the condition that the power switch 93 of the ophthalmic apparatus 1 is turned on, the examiner sets the subjective eye inspection mode by using the switch unit 95 and then depresses the separate chart switch 74e of the switch panel 73 to interpose the separate chart 501 into the optical path of the gazing target system 3.

Under this condition, the visible light having the wavelength of from 400 to 700 nm emitted by the light source 30 of the gazing target system 3 is collected by the condenser lens 31 and then illuminated on the separate chart 501 in the chart plate 32a.

The light passed through the marks 501a and 501b of the separate chart 501 is formed into a pair of rays of light in the separate condition by the respective prisms 502a and 502b of the split prism 502. The pair of rays of light are merged into the measuring optical system 21 of the objective refractive measuring system 2 through the projection lens 35, the mirror 36 and the mirror 217, pass the filter 215 through the focusing lens 216, and are introduced into the mirror 212 through the mirror 214 and the relay lens 213. The pair of rays of light are diaphragmed by the pair of through holes 503a and 503b of the diaphragm 503 arranged corresponding to the pair of separately arranged marks 501a and 501b constituting the separate chart 501 shown in FIG. 6 and then are introduced into the variable cross cylinder 37.

The pair of rays of light passed through the variable cross cylinder 37 is reflected by the mirror 38 and the mirror 111, projected to the eye E to be examined by the objective lens 110 and observed by the eye E to be examined.

In this case, when the person to be examined depresses a plus button or a minus button of the mouse 96 by his or her finger, the lens driver unit 320 causes the optical unit 219 to move on the basis of the control of the CPU 310 in response to the signal from the mouse 96, so that the position of the focusing lens 216 is shifted in the plus direction (+) or the minus direction (−) along the optical axis, as shown in FIG. 6.

Figure 8A:
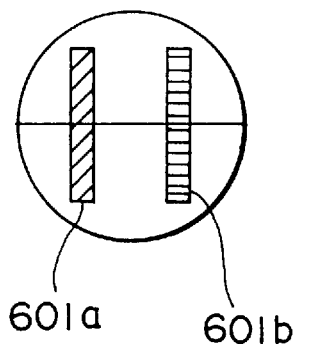
FIGS. 8A to 8C show the observation condition of the separate chart to the eye in the ophthalmic apparatus according to the embodiment.
Figure 8B:
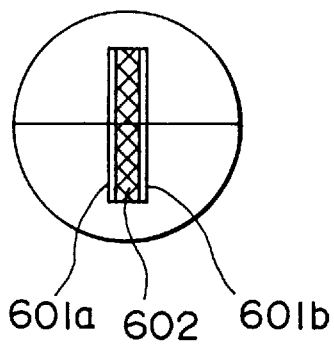
Figure 8C:
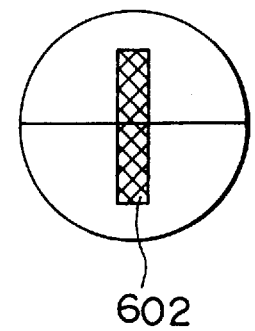

As a result, as shown in FIGS. 8A to 8C, the images of the pair of separately arranged marks 501a and 501b observed by the eye E to be examined are changed from the condition that the images 601a and 601b of the marks 501a and 501b are separated right and left to the condition that the images are partially overlapped with each other or completely identical with each other. In FIGS. 8A to 8C, the image 601a of the mark 501a is indicated by the oblique lines representing the red color, and the image 601b of the mark 501b is indicated by the horizontal lines representing the green color.

As shown in FIGS. 8C, under the condition that the images of the marks 501a and 501b are identical with each other, it means that the marks 501a and 501b are in conjugative relation with the fundus ER of the eye E to be examined. Thus, the eye E observes a white color image 602 (indicated by cross oblique lines) where the green color and the red color are mixed with each other. In this case, the eye E to be examined may be observe the far-sight position (zero diopter in an emmetropia eye) at which the adjustment force does not work in the eye E.

Also, when the position of the focusing lens 216 is changed in the minus direction along the optical axis by the operation of the mouse 96, the limit position where the images 601a and 601b of the marks 501a and 501b are displaced to both sides of the image 602, as shown in FIG. 8B, means the limit for the adjustment force (several diopters) of the eye-E to be examined, i.e., the near-sight position shifted by several diopters from the subjective measurement value obtained in the far-sight position.

Thus, the conditions of eye E to be examined for the far-sight position and the near-sight position in the above conditions are automatically measured by the gazing target system 3. A spherical degree S, a cylindrical degree C and an axis angle A are obtained by the operation of the image processing unit 71 and the arithmetic-logic unit 330 and these values are displayed on the display unit 72.

As described above, the person to be examined may perform the subjective measurement of the eye E to be examined by himself or herself while observing the images 601a and 601b and the image 602.

As shown in FIG. 8C, in the condition that the images of the marks 501a and 501b are completely identical (overlapped) with each other and the eye to be examined E observes the white color image 602 (indicated by cross oblique lines), the person to be examined operates, for example, the plus button of the mouse 96 so that the optical unit 219 is moved by the lens driver unit 320. Thus, on the basis of the control of the CPU 310 the lens driver unit 320 moves the optical unit 219, so that the focusing lens is fogged by a fog amount to be continuously predetermined. As a result, the person to be examined operates the mouse 96 to perform the precise measurement of the spherical degree of the eye E to be examined.

A concrete example of the precise measurement for the spherical degree of the eye to be examined E will now be described in detail with reference to FIGS. 9 to 12. FIG. 9 shows a schematic optical path of an ophthalmic apparatus 1 when the eye to be examined E is set at a zero diopter (0D). FIG. 10 shows a schematic optical path of an ophthalmic apparatus 1 when the eye E to be examined is set at −5 diopter (−5D).

Assume that the objective measurement value of the spherical degree S of the eye to be examined E when the above measurement is carried out for the eye to be examined E be −5 diopter. In this case, as shown in FIG. 10, the separate chart 501 is fixed, for example, for about one second at the position where the objective measurement value of the spherical degree S of the eye E to be examined is at −5D.

Thereafter, in the same way as described above, the lens driver unit 320 is controlled by the CPU 310 and thus the focusing lens 216 of the optical unit 219 is continuously fogged so that the spherical degree S is changed by +0.25D. An astigmatism degree C and axis angle A are constant. The amount x of the movement of the focusing lens 216 at this time may be obtained by the formula $x=f\times D/(100-15D)$ where D is the refractive index, the amount x of movement is the amount of movement with reference to 0D, f is the composite focal length of the focusing lens 216 and the relay lens 213.

The relationship between the fog amount in the case where the fogging is effected through four steps by +0.25D and the objective measurement result through the ophthalmic apparatus 1 is shown in FIG. 11.

As is apparent from FIG. 11, in the fogging in the four steps, the objective measurement value for the spherical degree S for any one after the second fogging is −0.00D. Accordingly, the objective measurement value for the spherical degree S for the fogging in the second step represents the limit of the adjustment force of the eye E to be examined.

The amount of fogging and the objective measurement result of the ophthalmic apparatus 1 are automatically measured by the gazing target system 3. The spherical degree S, the astigmatic degree C and the axis angle A are obtained by the image processing unit 71 and the arithmetic-logic unit 72. These values are displayed on the display unit 72 and simultaneously printed by the printer 90 as shown in FIG. 12.

In this case, if the mark representing a limit of the adjustment force of the eye E to be examined is printed in a position of the objective measurement value S−0.00D of the spherical degree S for the second fogging out of the four step foggings, the person to be examined may, at glance, know the complete correction value representing the limit of the adjustment force of the eye E to be examined. Therefore, in a basis of the complete correction value, the subjective comfortable degree for the new spectacle lens can be estimated in view of the spherical degree, the cylindrical degree and the axis degree of the spectacle lens for the current use of the person to be examined.

It is possible to change and modify the present invention within the scope of the claims in addition to the above-described specific embodiment.

According to the present invention, it is possible to provide an ophthalmic apparatus which may precisely measure the limit of the adjustment force of the eye to be examined.

Also, according to the present invention, it is possible to provide an ophthalmic apparatus which may estimate the subjective comfortable degree of the eye to be examined and select the suitable spectacle lens.

What is claimed is:

1. An ophthalmic apparatus comprising:

an objective refraction measuring system for measuring a refractive power of an eye to be examined in an objective manner;

a gazing target system having a gazing chart fixed to the eye;

means for detecting a far-sight position of the eye by the gazing target system; and fogging means for setting the gazing chart to the detected far-sight position and fogging the set gazing chart, wherein a continuous objective measurement is performed by the objective refraction measuring system while fogging the set gazing chart by the fogging means.

2. An ophthalmic apparatus comprising:

objective measuring means for measuring objective measurement values of an eye to be examined;

gazing chart fixing means for fixing a gazing chart to the eye;

means for detecting a far-sight position of the eye by the gazing chart fixing means;

fogging means for setting the gazing chart to the detected far-sight position of the eye and fogging the set gazing chart by desired fogging amounts, to perform a continuous objective measurement by the objective measuring means; and output means for outputting the fogging amounts of the gazing chart in the continuous objective measurement and the objective measurement values measured by the objective measuring means.

3. The apparatus according to claim 2 wherein a subjective comfortable degree for a spectacle lens is estimated in accordance with constant objective measurement values output from the output means.

4. The apparatus according to claim 3 wherein the objective measurement values output from the output means include an objective measurement value in a spherical degree of the eye.

5. The apparatus according to claim 3 wherein a limit of an adjustment force of the eye is obtained in accordance with the objective measurement values measured at the desired fogging amounts.

6. An ophthalmic apparatus comprising:

objective measuring means for measuring objective measurement values of an eye to be examined;

gazing chart fixing means for fixing a gazing chart to the eye;

means for detecting a far-sight position of the eye by the gazing chart fixing means; and fogging means for setting the gazing chart to the detected far-sight position of the eye and fogging the set gazing chart by desired fogging amounts, to perform a continuous objective measurement by the objective measuring means.

7. The apparatus according to claim 6 wherein the objective measurement values measured by the objective measuring means include an objective measurement value in a spherical degree of the eye.

8. The apparatus according to claim 6 wherein a limit of an adjustment force of the eye is obtained in accordance with the objective measurement values measured at the desired fogging amounts.

* * * * *

UNITED STATES PATENT AND TRADEMARK OFFICE
CERTIFICATE OF CORRECTION

PATENT NO. : 5,844,661
DATED : Dec. 1, 1998
INVENTOR(S) : Saeko Uchida, et al.

It is certified that error appears in the above-identified patent and that said Letters Patent is hereby corrected as shown below:

On the cover page, Line [73], should also list --Kabushiki Kaisha, Miki, Tokyo, Japan--.

Signed and Sealed this

Fourteenth Day of September, 1999

Attest:

Q. TODD DICKINSON

*Attesting Officer*    *Acting Commissioner of Patents and Trademarks*